(12) United States Patent
Lawaczeck et al.

(10) Patent No.: US 7,672,431 B2
(45) Date of Patent: Mar. 2, 2010

(54) X-RAY ARRANGEMENT AND X-RAY CONTRAST PROCESS FOR IMAGING AN OBJECT UNDER EXAMINATION THAT CONTAINS AT LEAST ONE RADIOPAQUE ELEMENT AS WELL AS USE OF THE X-RAY ARRANGEMENT

(75) Inventors: Ruediger Lawaczeck, Berlin (DE); Andreas Muehler, Mountain Lakes, NJ (US); Hanns Joachim Weinmann, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 10/961,377

(22) Filed: Oct. 12, 2004

(65) Prior Publication Data

US 2005/0123093 A1    Jun. 9, 2005

Related U.S. Application Data

(60) Provisional application No. 60/512,764, filed on Oct. 21, 2003.

(30) Foreign Application Priority Data

Oct. 10, 2003   (DE) ................................. 103 47 961

(51) Int. Cl.
  *H05G 1/64* (2006.01)
(52) U.S. Cl. ........................................ 378/98.11; 378/5
(58) Field of Classification Search ................ 378/98.8, 378/98.9, 98.11, 5, 156, 98.12
  See application file for complete search history.

(56) References Cited

U.S. PATENT DOCUMENTS

| | | | |
|---|---|---|---|
| 3,974,386 A | | 8/1976 | Mistretta et al. |
| 4,686,695 A | * | 8/1987 | Macovski .................... 378/146 |
| 4,736,398 A | | 4/1988 | Graeff et al. |
| 4,890,310 A | | 12/1989 | Umetani et al. |
| 4,945,552 A | * | 7/1990 | Ueda et al. ................ 378/98.11 |
| 5,049,746 A | | 9/1991 | Ito et al. |
| 5,434,417 A | | 7/1995 | Nygren et al. |
| 5,500,534 A | * | 3/1996 | Robinson et al. ......... 250/385.1 |

(Continued)

FOREIGN PATENT DOCUMENTS

DE    100 33 497    1/2002

(Continued)

*Primary Examiner*—Jurie Yun
(74) *Attorney, Agent, or Firm*—Millen, White, Zelano, Branigan, P.C.

(57) ABSTRACT

To increase the contrast in the imaging in an object under examination that contains at least one radiopaque element, an arrangement that has the following features is used: a) at least one essentially polychromatic x-ray radiation source that emits x-ray radiation, b) at least one energy-dispersive detector, with which the intensity of the x-ray radiation that gets through the object under examination is detectable, c) at least one correlation unit, with which the intensity of the detected x-ray radiation from a pixel of the object under examination with a first energy $E_1$ can be correlated with the intensity of the detected x-ray radiation from the same pixel with a second energy $E_2$, d) at least one output unit for visualizing the object under examination from the pixel signals that are obtained by correlation of the intensities.

44 Claims, 7 Drawing Sheets

U.S. PATENT DOCUMENTS

Figure 1:
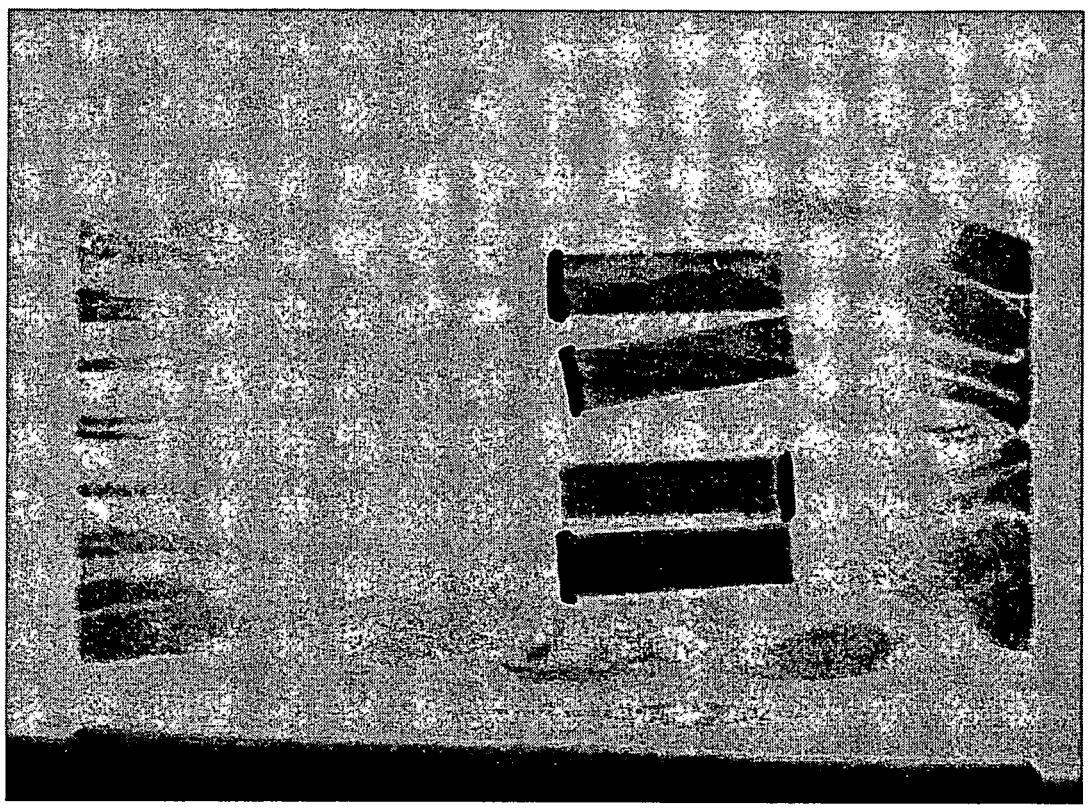

| | | | |
|---|---|---|---|
| 6,118,854 A * | 9/2000 | Solomon et al. | 378/156 |
| 6,393,097 B1 | 5/2002 | Aufrichtig et al. | |
| 6,891,918 B2 * | 5/2005 | Drummond et al. | 378/5 |
| 6,904,310 B2 * | 6/2005 | Knapp et al. | 600/431 |
| 6,922,462 B2 * | 7/2005 | Acharya et al. | 378/98.11 |
| 2005/0058242 A1 * | 3/2005 | Peschmann | 378/57 |

FOREIGN PATENT DOCUMENTS

| | | |
|---|---|---|
| DE | 101 18 792 | 11/2002 |
| WO | WO 02/052504 | 7/2002 |

* cited by examiner

X-RAY ARRANGEMENT AND X-RAY CONTRAST PROCESS FOR IMAGING AN OBJECT UNDER EXAMINATION THAT CONTAINS AT LEAST ONE RADIOPAQUE ELEMENT AS WELL AS USE OF THE X-RAY ARRANGEMENT

This application claims the benefit of the filing date of U.S. Provisional Application Ser. No. 60/512,764 filed Oct. 21, 2003.

DESCRIPTION

The invention relates to an x-ray arrangement for imaging an object under examination that contains at least one radiopaque element, the use of the x-ray arrangement for graphic display of an object under examination by means of x-ray radiation, as well as an imaging x-ray contrast process on the object under examination, for example a mammal, especially a human.

The medical diagnosis with the aid of x-ray radiation is a technically highly-developed field for diagnosis of diseases, for example for early detection, for radiographic identification, for characterization and for location of tumors of the female breast. The technique is very efficient and exhibits high availability.

To produce x-ray radiation, x-ray tubes, for example with W—, Mo— or Rh— rotating anodes and Al—, Cu—, Mo— and Rh filters, are available. With suitable filtration, a portion of the bremsstrahlung is filtered out, such that in advantageous cases, essentially the characteristic radiation emerges from the x-ray tubes.

As detectors, either conventional x-ray films or, recently, also digital flat-bed detectors are used. Instead of x-ray films, phosphorus displays (digital plates) can also be used. The image that is produced in these displays by the incident x-ray radiation can be enhanced in x-ray image intensifiers. In PIITV technology (phosphorus-image-intensifier technology), the enhanced image is transmitted via a very quick optical system to a videocamera. In the PPCR (Photostimulable Phosphor Computer Radiography), a digital display that is constituted by a layer that consists of $BaFX:Eu^{2+}$ crystals is used, whereby X=Cl, Br, or I. The image that is produced in the display is latent and is read out by an IR laser, for example an He—Ne laser, whereby luminescence in the UV range is produced. The UV light is collected with a fiber optic light guide, directed into a photomultiplier and converted into digital signals (U.S. Pat. No. 5,434,417 A). For direct conversion of x-ray radiation into electric signals, semiconductor detectors that consist of cadmium-zinc-telluride (CZT), amorphous salts or amorphous or crystalline silicon are used (M. J. Yaffe, J. A. Rowlands, "X-Ray Detectors for Digital Radiography," *Med. Biol.*, 42(1) (1997) 1-39). An example of the design of such detectors is indicated in U.S. Pat. No. 5,434,417 A. To also make possible an energy sensitivity of the detector, the latter is formed from several layers. X-ray radiation with different energy penetrates in different depths in this detector and produces an electric signal in the respective layer by photoelectric effect, which can be read out according to the layer and thus according to the energy of the x-ray photons, immediately identifiable as a current impulse.

Computer tomography (CT) has already been used for a long time as a routine process in regular clinical practice. With CT, sectional images through the body are obtained, with which a better spatial resolution is achieved than with the usual projection radiography. Although the density resolution of the CT is also clearly higher than the density resolution of the conventional x-ray technology, contrast media are still required for reliable detection of many pathological changes.

In many cases, the conventional x-ray technology could not be used, since the contrast of the tissue to be examined was not adequate. For this purpose, x-ray contrast media were developed that produce a high radiographic density in the tissue, in which they accumulate. Typically, iodine, bromine, and elements of atomic numbers 34, 42, 44-52, 54-60, 62-79, 82 and 83 are proposed as opacifying elements as well as the chelate compounds of the elements with atomic numbers 56-60, 62-79, 82 and 83. As iodine compounds, for example, meglumine-Na- or lysine-diatrizoate, iothalamate, ioxithalamate, iopromide, iohexol, iomeprol, iopamidol, ioversol, iobitridol, iopentol, iotrolan, iodixanol and ioxilan (INN) can be used (EP 0 885 616 A1).

In some cases, despite the administration of x-ray contrast media, no adequate tissue contrast could be achieved. To achieve an additional increase in the contrast, digital subtraction angiography (DSA) was introduced. This process, however, did not gain acceptance for the visualization of lesions of the female breast, since the reliability and sensitivity for many applications turned out to be too low, and in any case, an additional examination was necessary (P. B. Dean, E. A. Sickles, *Invest. Radiol.*, 20 (1985) 698-699).

Another subtraction method for use in mammography is disclosed in EP 0 885 616 A1: For projection mammography, it is proposed there first to take a pre-contrast mammogram, then the patient is to be quickly injected i.v. with a commonly used urographic x-ray contrast medium, and a post-contrast mammogram is to be taken about 30 seconds to 1 minute after the end of the injection. The data that are obtained from the two images are then correlated with one another, preferably subtracted from one another.

This subtraction process, however, represents a considerable exposure of the patient, since two images, taken at different times, must be prepared, whereby the first image is obtained before the injection of the contrast medium, and the second image is obtained up to 5 minutes after the injection. During this time, the breast of the patient is clamped to avoid artifacts of movement. This is possible during the above-mentioned long time span, but only incompletely. In addition, the securing of the breast causes the patient pain. In the same way, because of the risk of artifacts of movement, the DSA is also disadvantageous since a complete freedom from moment is hardly attainable. Thus, to date, aside from a few CT studies, radiographic studies of the female breast supported by contrast media have not been successful.

New developments in the field of CT relate to the excitation side, for example, the use of synchrotron radiation in CT (F. A. Dilmanian, "Computed Tomography with Monochromatic X-Rays," *Am. J. Physiol. Imaging*, 314 (1992) 175-193). Good x-ray images are obtained, for example, by means of "K-Edge Subtraction CT" (F. A. Dilmanian, op. cit., page 179), whereby the strong increase of the absorption coefficient in the binding energy of the K-electron of an atom is used. The element iodine has a K-edge at an energy of 33.17 keV. The increase of the absorption coefficient on this edge is strong enough to obtain good images from the difference of two measurements with energies just above and just below this edge. In this case, the procedure is that an iodine-containing x-ray contrast medium is administered to the patient before the x-ray study. A short time later, two x-ray images are recorded at two different wavelengths (energies) of the x-ray radiation. The two x-ray images (or the two intensities) can then be subtracted from one another. As a result, an image with a much better resolution is obtained than in the conventional recording of an x-ray image.

Unfortunately, this process works only with the aid of the synchrotron radiation that is available to large storage rings, such as, for example, with DESY, since only this radiation has the monochromasia and intensity that are advantageous for the process. Conventional x-ray tubes do not yield any monochromatic radiation but rather a continuous spectrum. They are therefore not readily suitable for such measurements of difference.

An alternative possibility is described in DE 101 18 792 A. To take projection mammograms, a process is proposed in which x-ray radiation sources with two x-ray anodes made of different materials are used. To take the mammogram, first an x-ray contrast medium is administered to the patient. Then, a first projection mammogram is taken with use of the first of the two x-ray anodes and then a second projection mammogram is taken with use of a second x-ray anode. By the superposition of each individual pixel from the first mammogram with each individual corresponding pixel from the second mammogram, a correlation image is then created. The characteristic radiation of the two x-ray anodes is matched to the absorption spectrum of the x-ray contrast medium: the emission energy of the first x-ray anode lies slightly below the absorption energy of the opacifying element in the x-ray contrast medium and the emission energy of the second x-ray anode lies slightly above the absorption energy of the opacifying element.

A drawback of this process consists in the fact that conventional x-ray tubes cannot be used with only one x-ray anode. In addition, the proposed arrangement is inflexible with respect to the x-ray contrast medium that is to be used, since the opacifying element in the x-ray contrast medium is determined by a preset selection of the two x-ray anodes in an x-ray radiation source. If, in the case of varying requirements, different x-ray contrast media with different opacifying elements must be used, it is necessary also to exchange the x-ray radiation source to match the x-ray anodes to the altered opacifying element.

In addition, in DE 100 33 497 A1, an x-ray contrast process for producing an element-selective x-ray contrast by digital absorption edge subtraction of two contrast images at energies above and below the absorption edge of the contrast element is described. To perform the process as a radiation source, a microfocus tube with exchangeable anode or anticathode materials is used, whose point focus produces a divergent beam for a central projection of the object to be imaged. To produce images, the characteristic radiation of the microfocus tubes as well as an energy-selective site-resolving x-ray detector are used as in the case of the arrangement of DE 101 18 792 A1.

This process also exhibits the drawback that different x-ray anodes are to be used under varying requirements with respect to the x-ray contrast medium to be used. In such cases, it is therefore necessary to exchange one x-ray anode for another. This is complicated and virtually not implemented in mammography except for the special case of a bi-anode tube. In general, the individual x-ray anodes also require different voltages, such that optionally even several electrical supplies must be held back to be able to produce x-ray images with different x-ray contrast.

The problem of this invention is therefore to avoid the above-mentioned drawbacks and to find in particular arrangements and processes with which images can be produced with different radiopaque elements without considerable equipment. Further, the x-ray images are also to be able to be taken in a simple, easy way, without high costs resulting. The technology is to be available on a wide basis. Also, smaller lesions in the body of the object under examination are to be made visible with the smallest possible radiation dose in high site resolution. Also, artifacts of movement, which are produced by taking images made at different times, are to be reliably avoided.

This problem is solved by the x-ray arrangement for imaging an object under examination that contains at least one radiopaque element according to the following, the use of the x-ray arrangement according to the following, and the imaging x-ray contrast process according to the following. Preferred embodiments of the invention are indicated in the subclaims.

The invention can be used in particular for studying humans. The invention is suitable for the production of projection radiographs for visualization of masses, vessels and perfusions, for example for visualization of the esophagus-stomach-intestine passage, for bronchography, cholegraphy, angiography and cardiography, for cerebral angiography and for perfusion measurements, for mammography, lymphography, and for quantification of lime deposits and bone densities. The invention can also be extended to computer tomography. In principle, the invention can also be used to study non-living materials, for example in the field of materials testing.

To achieve the object, the object under examination is irradiated with polychromatic x-ray radiation and the radiation that gets through the object is measured with a digital detector, whereby the detector is also able to determine the energy of the incident photons.

In this respect, the x-ray arrangement according to the invention has the following features:

a. At least one x-ray radiation source that emits essentially polychromatic x-ray radiation, b. At least one energy-dispersive detector, with which the intensity of x-ray radiation that gets through the object under examination can be detected, c. At least one correlation unit, with which the intensity of the detection x-ray radiation from a pixel of the object under examination with a first energy $E_1$ (e.g., with an energy above an absorption edge of the opacifying element of the opacifying element) can be correlated with the intensity of the detected x-ray radiation of the same pixel with a second energy $E_2$ (e.g., with an energy below the absorption edge of the opacifying element), d. At least one output unit for visualizing the object under examination from the pixel signals obtained by correlation of the intensities.

The x-ray arrangement is used primarily for the graphic display of an object under examination by means of x-ray radiation. The opacifying element that is contained in the object under examination can originate from the elements that are naturally contained in the object or can be introduced by an x-ray contrast medium. The x-ray arrangement is used to perform the x-ray contrast process according to the invention. The process has the following process steps:

a. Irradiation of the object under examination that contains at least one radiopaque element with essentially polychromatic x-ray radiation, b. Energy-dispersive detection of the intensity of the x-ray radiation that gets through the object under examination, c. Correlation, i.e., mathematical linkage, of the intensities of the detected x-ray radiation from a pixel of the object under examination with a first energy $E_1$ (e.g., with an energy above an absorption edge of the opacifying element) with intensities of the detected x-ray radiation of the same pixel with a second energy $E_2$ (e.g., with an energy below the absorption edge of the opacifying element), d. Visualization of the object under examination from pixels that are obtained by correlation of the intensity values.

To determine the intensities and the energy of the x-ray radiation that gets through the object under examination, the detected photons are divided into at least two different energy ranges, for example those that are a little below and those that are a little above an absorption edge in the absorption spectrum of the opacifying element.

With the x-ray arrangement according to the invention and the process according to the invention, soft tissue can also be visualized in high contrast in the human. By matching the energy, measured by the detector, of the x-ray radiation that gets through the object under examination to the type of opacifying element, an efficient increase in contrast relative to the conventional process can be achieved, whereby the drawbacks of the arrangements and processes (reduced flexibility), described in DE 101 18 792 A1 and DE 100 33 497 A1, need not be tolerated. The process is simple to implement and has a broad field of application.

To generate the x-ray radiation, a normal, commercially available x-ray tube with a continuous spectrum can be used, for example a tube with an Mo, W or Rh anode. The continuous spectrum is produced by a corresponding voltage on the x-ray tube. Depending on the type of opacifying element that is contained in the object under examination, a voltage is applied that makes possible an emission of the continuous radiation in the range up to, for example, over 100 keV.

In principle, the x-ray radiation source can be operated without filtering the emitted radiation, such that polychromatic radiation occurs in the entire spectral range on the object under examination. To reduce the radiation exposure of the object under examination, however, it is also possible to filter out such x-ray radiation from the spectrum of the polychromatic x-ray radiation source, whose energy is not necessary or is not advantageous for the detection. To this end, for example, an Al or a Cu filter is used, which filters out energies in the range of $\leqq 20$ keV (soft radiation). Defined as a continuous spectrum is thus an x-ray emission in a range of $\geqq 0$ keV, preferably $\geqq 15$ keV, especially preferably $\geqq 17$ keV, and quite especially preferably $\geqq 20$ keV, up to, for example, 100 keV, whereby no spectral range within these limits compared to others is emphasized or excluded. The upper limit of the emission spectrum is determined by the voltage that is applied to the x-ray anode. The low-energy range of the radiation is preferably filtered out to eliminate the dose-relevant radiation for the human body.

If a native x-ray contrast is ignored, an x-ray contrast medium is administered to the object under examination, for example a human, to perform the process according to the invention. The x-ray contrast medium can be administered, for example, enterally or parenterally, especially by i.v., i.m. or subcutaneous injection or infusion. Then, the x-ray image is made. Those x-ray contrast media that exhibit in particular a strong increase of the absorption coefficient on the K- or L-edge of the absorption spectrum are suitable. Such x-ray contrast media contain opacifying elements with an atomic number of 35 or greater than 35—in this case, for example, this is a contrast medium that contains bromine—with an atomic number of 47 or greater than 47—in this case, this is a contrast medium that contains iodine—, with an atomic number of 56—in this case, this is a contrast medium that contains barium—, with an atomic number of 57 or greater than 57—in this case this is a contrast medium that contains lanthanides, especially contrast media that contain gadolinium—or with an atomic number of 83—in this case this is a contrast medium that contains bismuth. Therefore, x-ray contrast media that contain opacifying elements with an atomic number of 35 (bromine) to 83 (bismuth) are suitable. Especially suitable are contrast media with opacifying elements with an atomic number of 53 (iodine)—83 (bismuth). Also suitable are x-ray contrast media with opacifying elements with an atomic number of 56 (barium), 57 or greater than 57 (lanthanides)—83 (bismuth) and especially preferably agents with opacifying elements with an atomic number of 56-70 (barium, lanthanides: La, Ce, Pr, Nd, Pm, Sm, Eu, Gd, Tb, Dy, Ho, Er, Tm, and Yb).

Suitable iodine-containing x-ray contrast media are, for example, compounds that contain triiodine aromatic compounds, such as, for example, amidotrizoate, iohexol, iopamidol, iopanoic acid, iopodinic acid, iopromide, iopronic acid, iopydone, iotalaminic acid, iopentol, ioversol, ioxaglat, iotrolan, iodixanol, iotroxinic acid, ioxaglinicic acid and ioxitalaminic acid (INN). Trade names for x-ray contrast media that contain iodine are Urografin® (Schering), Gastrografin® (Schering), Biliscopin® (Schering), Ultravist® (Schering) and Isovist® (Schering).

Also suitable as x-ray contrast media are metal complexes, for example Gd-DTPA (Magnevist® (Schering)), Gd-DOTA (Gadoterate, Dotarem), Gd-HP-DO3A (Gadoteridol, Prohance® (Bracco)), Gd-EOB-DTPA (Gadoxetat, Primavist), Gd-BOPTA (Gadobenat, MultiHance), Gd-DTPA-BMA (Gadodiamide, Omniscan® (Amersham Health), Dy-DTPA-BMA, Gd-DTPA-polylysine, and Gd-DTPA-cascade polymers.

The K-edge of gadolinium is approximately 50.2 keV, i.e., far above the K-edge of iodine, which is approximately 33.2 keV. The metal complexes can also contain, instead of the gadolinium atoms, for example, lanthanum or dysprosium atoms.

Digital detectors have already been offered by various manufacturers for some time (for example: *The BBI Newsletter*, February 1999, page 34; H. G. Chotas, J. T. Dobbins, C. E. Ravin, "Principles of Digital Radiography with Large-Area, Electronically Readable Detectors: A Review of the Basics," *Radiol.*, 210 (1999) 595-599). They frequently consist of amorphous silicon or other semiconductor materials. In the x-ray arrangement according to the invention, i.a., the following detectors are suitable: detectors with phosphorus plates (for example from Fuji Chemical Industries, Konica), with amorphous silicon (for example from GE Medical, Philips Medical, Siemens Medical), with selenium (for example from Philips Medical, Toshiba), with gadolinium hyposulfite (for example from Kodak), with cadmium telluride or cadmium-zinc-telluride-(CZT) semiconductors, with yttrium oxyorthosilicate, with lutetium oxyorthosilicate, with sodium iodide or bismuth germanate. Especially good results are achieved with the so-called CZT detectors, i.e., detectors that consist of a cadmium-zinc-telluride-(CZT) semiconductor.

The design of an energy-dispersive detector, which is made from a semiconductor, is described in detail in U.S. Pat. No. 5,434,417 A. In this case, segmented semiconductor strips are provided that are irradiated from the front with x-ray radiation. The radiation penetrates the semiconductor material until it interacts with the semiconductor material. The penetration depth depends on the energy of the x-ray photons. With greater energy of the x-ray photons, the radiation penetrates more deeply, until it interacts with the detector material and generates a current impulse by a photoelectric effect, than with lower energy of the x-ray photons. The current impulses can be discharged in the individual segments of the detector by means of applied electric contacts. The current impulses are processed with an input amplifier.

On the one hand, the detector can be designed in the form of a flat-bed detector. In this embodiment, all pixels are detected simultaneously and passed on to the correlation unit for evaluation. In this case, the detector consists of a large-area arrangement of individual detector sensors, preferably in a matrix that has rows and columns of such sensors.

Instead of the flat-bed detector, a matrix of several detectors that are suitable for picking up an individual pixel can also be used. The x-ray radiation from the object under examination is simultaneously sent via an x-ray fiber optic light guide to these detectors. A number of such fiber optic light guides are combined in a surface detector.

In addition, the detector can be designed for picking up an individual pixel and can be movable so as to pick up all pixels. In this embodiment, the detector can detect only energy-dependent intensities in an individual pixel during the measurement. The intensities of the individual pixels are detected in succession, for example by lines, and are passed on to the correlation unit for further processing.

In addition, the detector can also have an array of detector sensors designed for picking up a pixel in each case and can be movable so as to pick up all pixels. In this embodiment, the detector detects the intensities of the individual pixels. To pick up all intensities, the detector is preferably moved perpendicular to the main axis of the array during the measurement. The intensities that are determined during the measurement are forwarded to the correlation unit.

The signal that originates from the input amplifier is then sent into at least one correlation unit, with which the intensity of the detected x-ray radiation from a pixel of the object under examination, for example with an energy above an absorption edge of the opacifying element, can be correlated with the intensity of the detected x-ray radiation of the same pixel, for example with an energy below the absorption edge of the opacifying element. The correlation unit can be a correspondingly programmed data-processing unit.

In the selection of a suitable x-ray contrast medium, x-ray photons that consist of two different energy ranges, which can be determined with the detector, are counted and correlated with one another in the correlation unit. The photons in the two energy ranges have energies that lie in a range that preferably extends from up to 5 keV below to 5 keV above the energy of the absorption edge of the opacifying element of the x-ray contrast medium, especially preferably from up to 3 keV above to 3 keV below the energy of the absorption edge. The closer the energies of the detected photons are to the absorption edge of the opacifying element that is being examined, the greater is the absolute difference of the energies of the photons in these two areas and the stronger becomes the signal that is used to produce the pixels.

To correlate the intensities of the photons of the two areas, the latter are correlated with one another a pixel at a time, preferably subtracted from one another or divided by one another. For example, first the logarithm of the measured intensities can also be taken, and subsequently subtracted. In all of these cases, intensities with energies are correlated with one another, which are preferably in a range of 1-5 keV below the absorption edge to 1-5 keV above the absorption edge of the opacifying element, which is present under native conditions in the tissue of the object under examination or is introduced by the x-ray contrast medium. To this end, in one case, a comparator can be used, and in the other case, a division term can be used for pixel correlation.

Of course, other mathematical operations can also be performed for correlation of the intensities of the x-ray radiation from a pixel that gets through the object under examination. For example, the intensity of the x-ray radiation in the immediate area of the absorption edge, for example in a range of ±2 keV relative to the absorption edge, can be measured in small steps, for example in 0.2 keV steps, and can be differentiated via the energy. To this end, a difference term can be used. In the area of the absorption edge, a large jump in the first derivative of the intensity is thus detected that appears as a significant signal in the pixel.

From the considerations above, it is clear that either the intensities of the x-ray radiation with certain energy values (in narrow energy intervals, for example ±0.2 keV) or the plot of the intensity over a certain spectral range (for example ±3 keV, relative to the absorption edge) are determined with the detector.

To be able to obtain the strongest possible signal from the areas in the object under examination in which x-ray contrast media are found, the intensities of the detected x-ray radiation are preferably detected below and above the K-edge of the absorption spectrum of the opacifying element. In principle, however, measurements in the area of the L-absorption edge or higher edges are also possible.

To process the measured intensities of a pixel, preferably the following devices that can be implemented in a data-processing unit are provided, namely:

e. A first storage unit, with which the intensities can be stored as a function of energy I(E) of individual pixels of the object under examination, f. A computing unit, with which intensity $I(E_1)$ of the detected x-ray radiation from a pixel of the object under examination, e.g., with an energy above an absorption edge of the opacifying element of an x-ray contrast medium, can be correlated with intensity $I(E_2)$ of the detected x-ray radiation from the same pixel, e.g., with an energy below the absorption edge of the opacifying element of the x-ray contrast medium, e.g., $I(E_1)/I(E_2)$, g. A second storage unit, with which the values obtained from the intensities of an individual pixel by correlation can be intermediately stored.

As a result, it is possible either first to detect the intensities of all pixels below or above the absorption edge, then all other intensities of all pixels, and then to pixel-correlate with one another and to use for imaging the measured data sets or alternately to measure and to correlate the respective intensities pixel by pixel and then to use the data that are obtained for imaging. To this end, the data that are obtained are delivered a pixel at a time to an output unit, which contains, for example, a monitor (cathode ray tube (CRT) or an LCD display) or a plotter.

Figure 2:
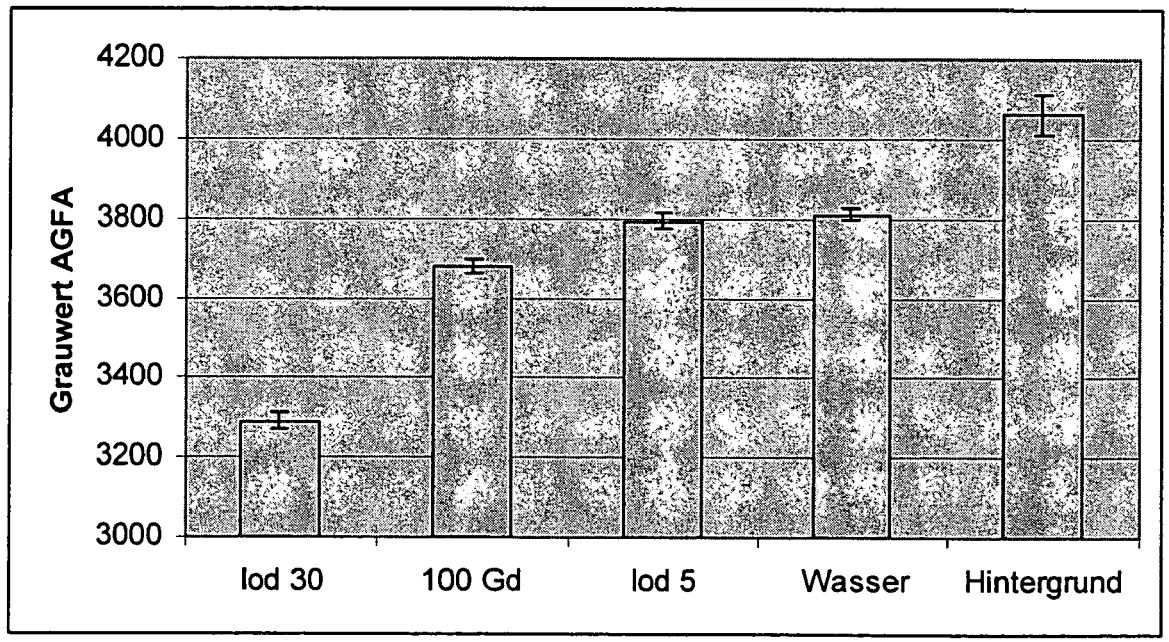
Figure 3:
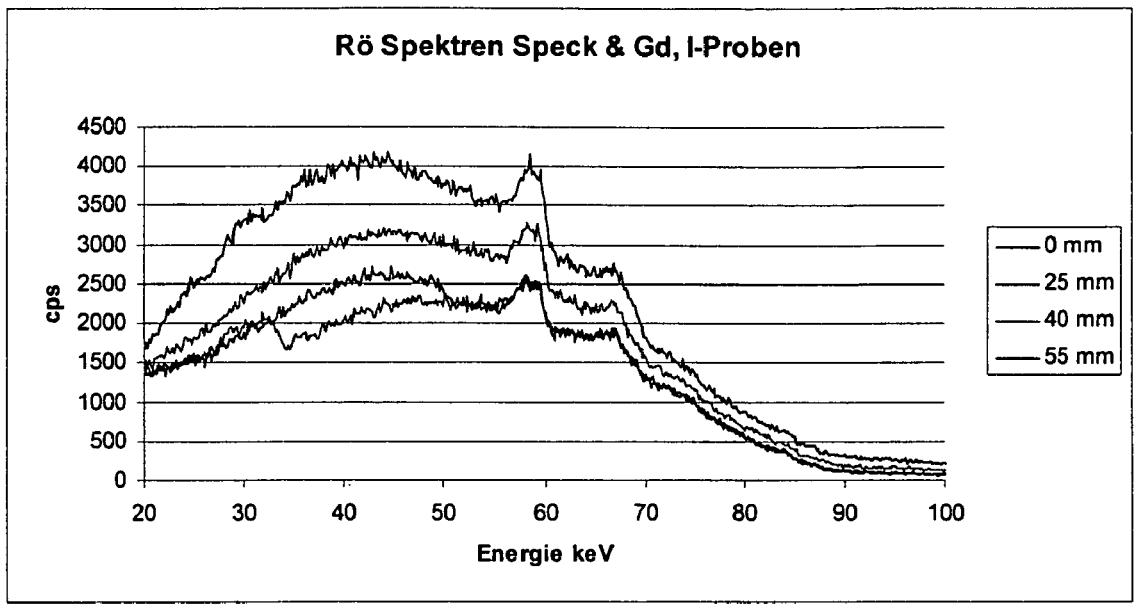
Figure 4:
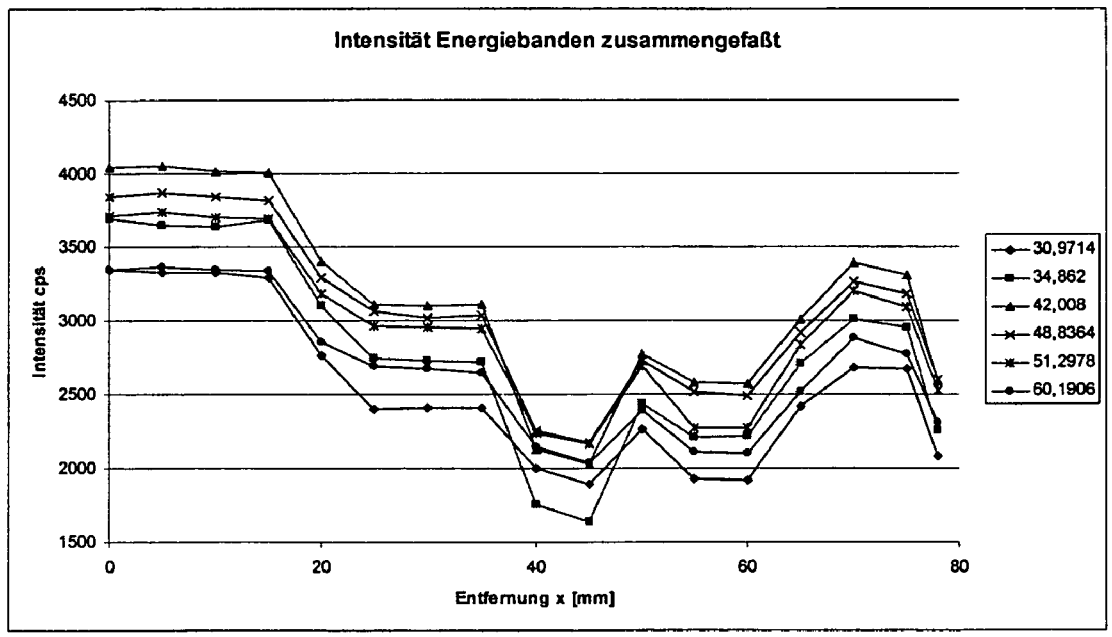
Figure 5:
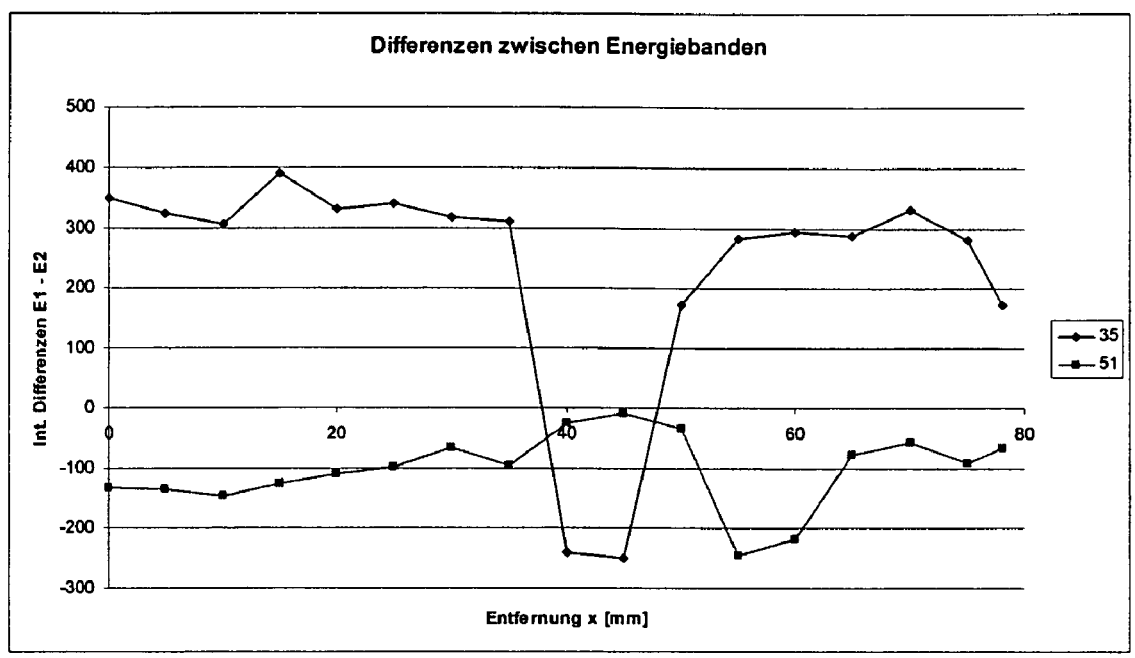
Figure 6:
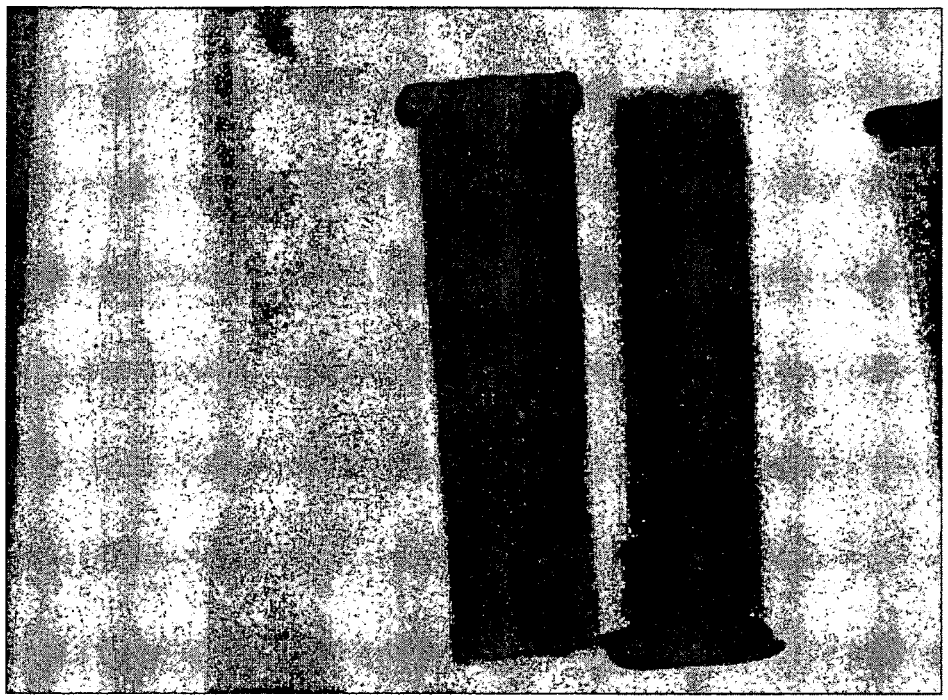
Figure 7:
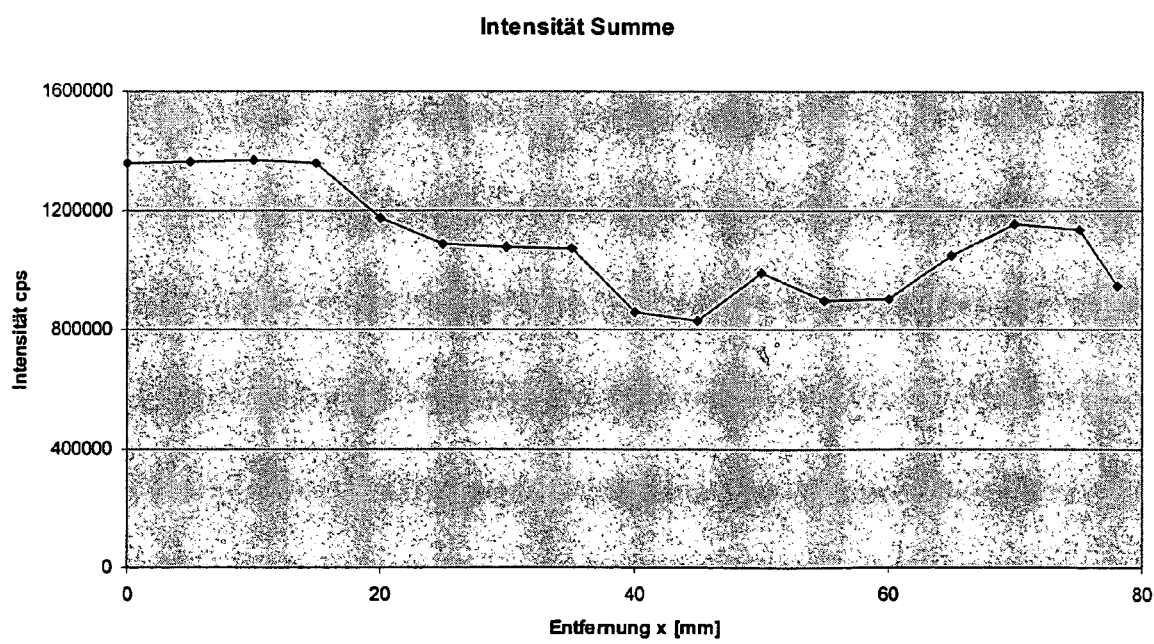
Figure 8:
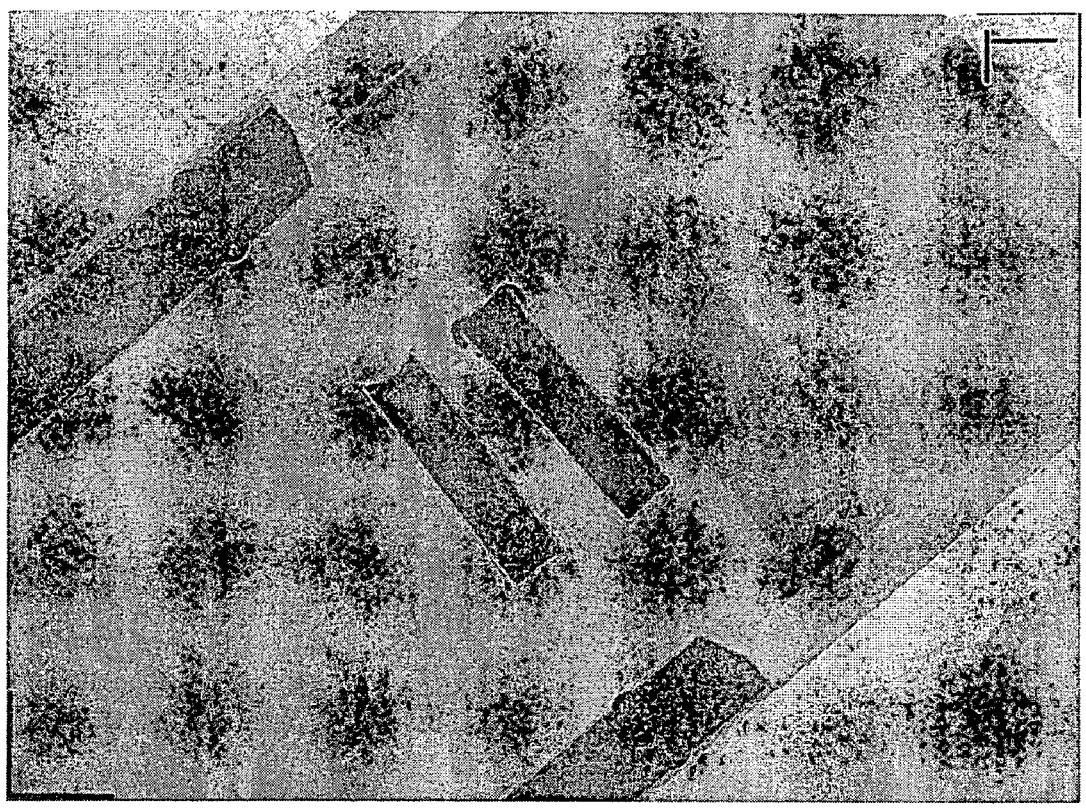
Figure 9:
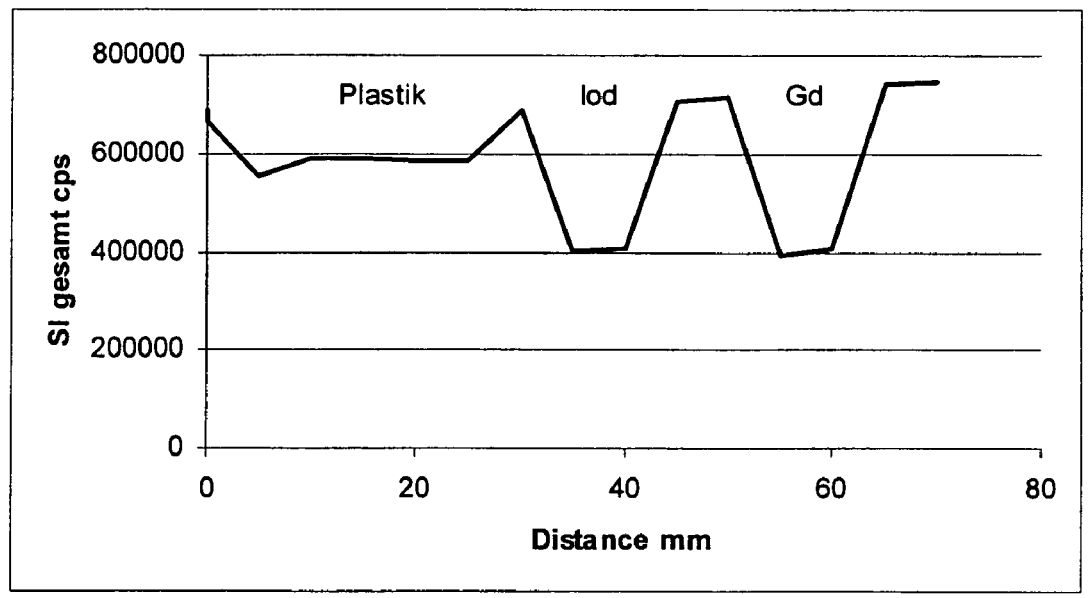
Figure 10:
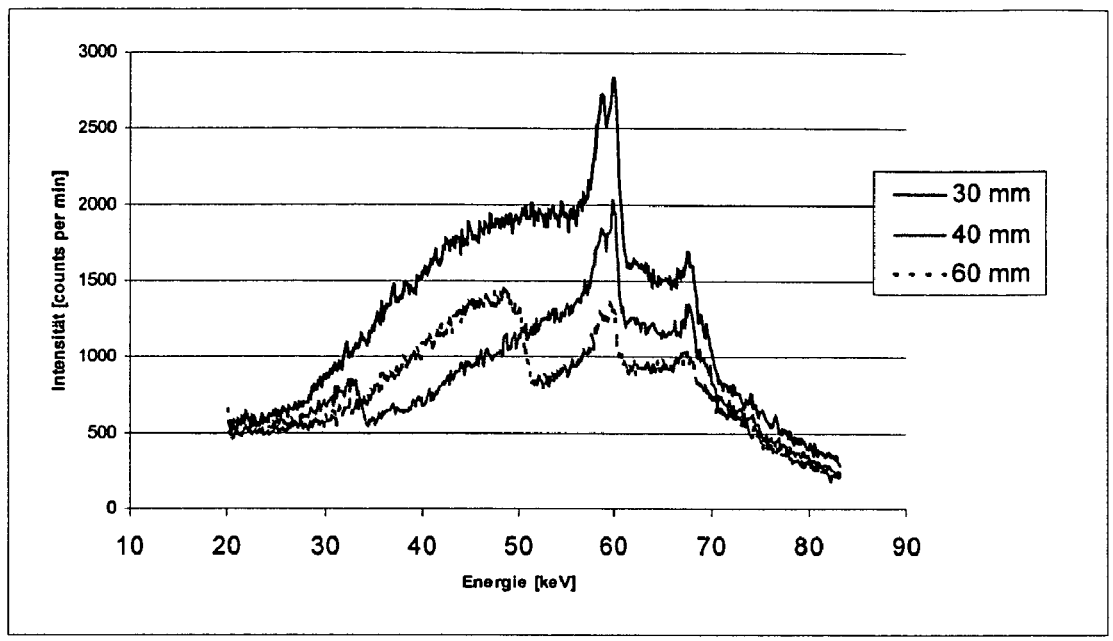
Figure 11:
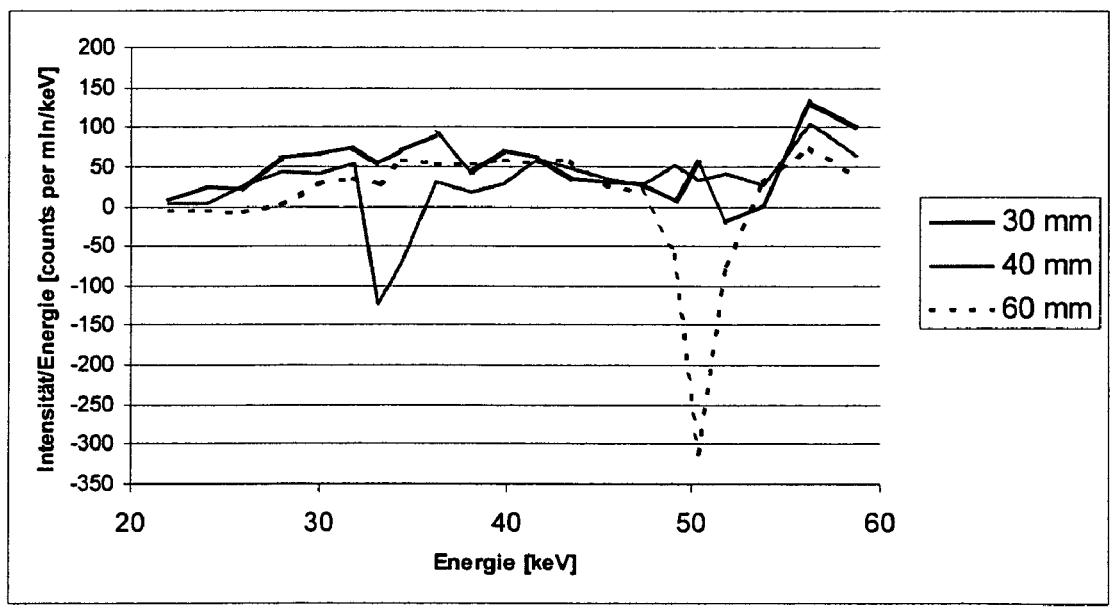

For the explanation of the invention below, the following figures and examples are used. In particular:

FIG. 1 shows a general view of a first phantom,

FIG. 2 shows a gray-scale analysis of the measuring samples in the first phantom, FIG. 3 shows spectra of samples of the first phantom, FIG. 4 shows x-ray radiation intensity in the area of two measuring cuvettes in the first phantom, FIG. 5 shows intensity differences above and below the K-edge of I or the K-edge of Gd in the first phantom, FIG. 6 shows a cross-section from the first phantom, FIG. 7 shows the total intensity plot in the cross-section area of FIG. 6, FIG. 8 shows a general view of a second phantom, FIG. 9 shows an attenuation of the overall signal intensity $SI_{ges}$ in the phantom of FIG. 7, FIG. 10 shows x-ray spectra at the 30 mm, 40 mm and 60 mm positions of the second phantom, FIG. 11 shows the first derivatives of the x-ray spectra of FIG. 10 according to the energy.

Figure 12:
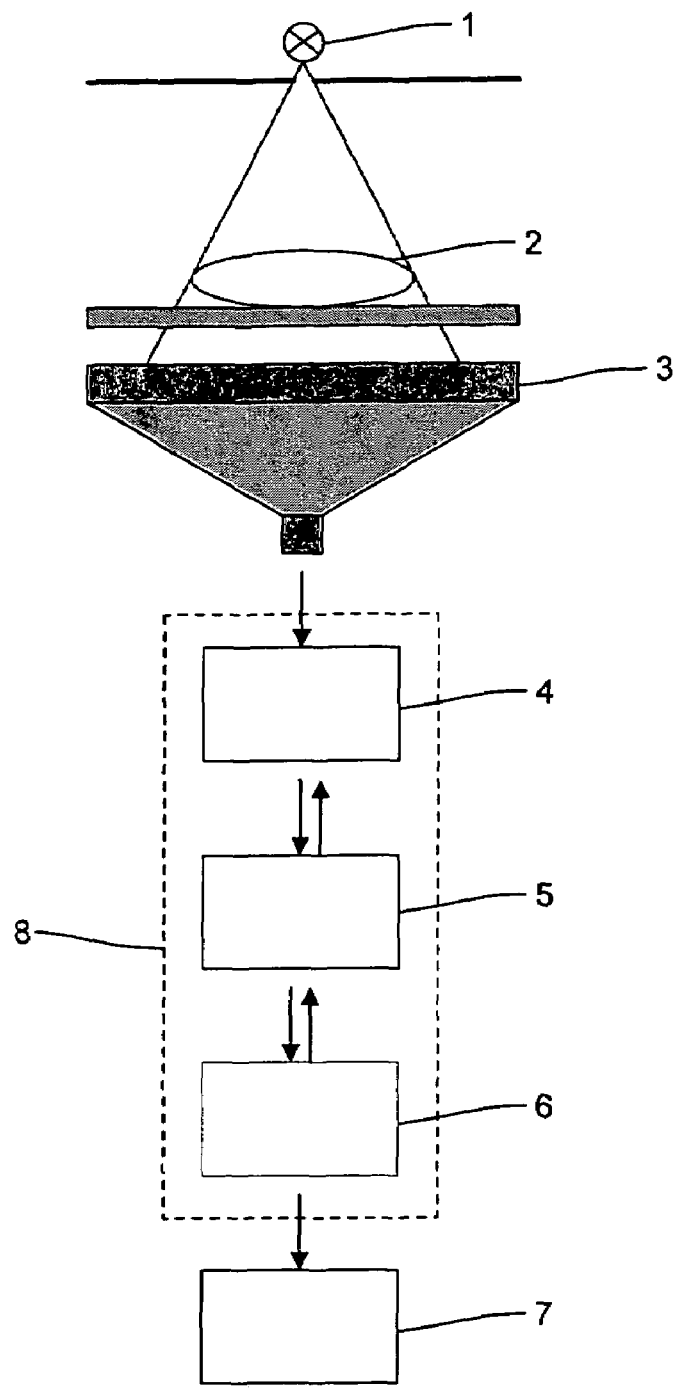

FIG. 12 depicts a radiation source (1), an object under irradiation (2), a (flat-bed) detector (3), a first storage unit (4), a computing unit (5), a second storage unit (6), an output unit (7) and a correlation unit (8).

EXAMPLE 1

For the visualization of a phantom, the following measuring design was selected:

The x-ray-radiation source was formed by an x-ray tube (10×15 tube) with a wolfram anode and a 4 mm thick Al filter. The x-ray source (RT250) was operated under the following operating conditions: 90 kV, 5 (10) mA, exposure time t=1 s. For detection of x-ray radiation, a CZT detector with a 3 mm×3 mm×2 mm cadmium-zinc-telluride crystal and 100/400 μm apertures was used (Amptek Inc., USA). The data were forwarded from the x-ray detector to a multichannel analyzer and then fed to an Excel spreadsheet. Signal intensities SI=SI(E) were thus available in digital form as a function of energy E.

The projection images were taken with a Siemens Polydoros x-ray tube, which was operated at 90 kV, 4 mAs, at a distance of 110 cm with AGFA digital plates. The gray-scale values at the desired positions were read out from the images digitally available to the work station.

The object under examination was a phantom that consisted of a 2 cm thick piece of streaky bacon on an acrylate glass base and four 1 cm plastic cuvettes arranged thereon, which were filled with 1) an aqueous solution containing 30 mg/ml of I (=236 mmol of I/l) (in the form of an iodine compound, Ultravist®),
2) an aqueous solution containing 100 mmol of Gd/L (in the form of a gadolinium compound, Gadovist®),
3) an aqueous solution that contains 5 mg/ml of I (in the form of an iodine compound),
4) water.

The phantom was brought into the beam path.

For optical visualization of the overall arrangement, first the detector was replaced by a phosphorus display (Agfa Image Plate), in which the projection image that was produced was latently stored in the form of trapped electrons and then was read out (made visible) with a laser. The arrangement that is recorded is indicated in FIG. 1. On the lower edge of the image, the acrylate glass plate can be detected by its edge. The streaky bacon is visible by the formation of streaks evident especially on the left and on the right edge. The darker structures that can be detected, for example, in the middle portion of the figure are the measuring cuvettes that contained—in the sequence from the bottom to the top—samples 1), 2), 3) and 4).

To determine the intensities of the x-ray radiation that gets through the measuring cuvettes, the gray-scale values from the read-out phosphorus screen were determined in the area of the cuvettes. The attenuation of the x-ray radiation by the cuvettes is depicted in FIG. 2. The bars indicate the respective gray-scale values in comparison to the background. The greatest attenuation of the radiation was obtained with the cuvette that contains 30 mg/ml of I. The sample with 5 mg/ml of I does not yield any significant difference in terms of attenuation compared to the cuvettes containing water.

To determine the spectral arrangement, the phantom was mounted via the detector on an x-y-plotting table. For relative movement of the phantom compared to the detector, the table was moved only in the x-direction.

First, spectra of the transmitted x-ray radiation were recorded at various sites under the phantom. To this end, the phantom was moved in steps of 5 mm in the x-direction via the fixed x-ray detector. For each x-location, an x-ray spectrum was recorded. The counting rate values determined by the detector were taken over as a function of the energy in Excel tables. As a result, an x,E-field (x=x-movement, E=energy) was obtained, whereby a signal intensity SI in [cps] was associated with each point (x, E). Only the range between 20 and 100 keV was considered. For better visualization, energy bands in which the measured SI were averaged over energy ranges were considered. The ranges are 22.5 keV, 32.3 keV, 34.2 keV, 40.9 keV, 51.2 keV and 56.9 keV. The ranges 22.5 keV, 40.9 keV and 56.9 keV lay outside the K-edges of the opacifying element I or Gd. With the inclusion of the K-edges, in addition the differences of the SI were formed, namely the differences $\Delta_1$=SI(E=34.2 keV)−SI(E=32.2 keV) and $\Delta_2$=SI(E=51.2 keV)−SI(E=49.2 keV). The overall signal intensity $SI_{ges}$ was also available.

In FIG. 3, spectra for air are shown at the x-coordinate position 0 mm (curve A), bacon at the x-coordinate position 25 mm (curve B), for the cuvette containing 30 mg/ml of I in aqueous solution at the x-coordinate position 40 mm (curve C) and for the cuvette containing 100 mmol of Gd in aqueous solution at the x-coordinate position 55 mm (curve D). The K-edges of I are readily visible at 33.2 keV and of Gd at 50 keV in the spectra recorded by the cuvettes.

In addition, the intensity in the detector was determined based on the displacement of the phantom with various detector energies. The curves are shown in FIG. 4. The individual curves had been recorded with various detector energies (curve A: 30.97 keV, curve B: 34.86 keV, curve C: 40.01 keV, curve D: 48.84 keV, curve E: 51.30 keV, curve F: 60.19 keV). The profile of the phantom is readily detectable. The site resolution of the scan is determined by the step width of 5 mm. The cuvettes are therefore not represented in the intensity plot by vertical flanks. The transparency increases with the x-ray energy. Exceptions are the K-edges, as can be detected in the difference image (FIG. 5). In FIG. 5, the differences of the signal intensities are formed and visualized with the energies that include the respective K-edge energy. The curve that is designated as 35 includes the iodine-K-edge, that designated as 51 referred to gadolinium. Based on the curve plot, it can clearly be seen that in one case, only iodine is visible, and in the other case, only Gd is visible. In the iodine curve (35), in addition to the pronounced signal change for the sample containing 30 mg of I/ml precisely in the middle of the image, the cuvette that contains 5 mg of I/ml is indicated on the right edge of the image.

To substantiate a correspondence between the profile of overall signal intensity $SI_{ges}$ and the arrangement of the phantom, a cross-sectional representation of the phantom was compared to the profile of overall signal intensity $SI_{ges}$. In FIG. 6, a cross-section from the phantom is shown with the aid of a phosphorus display (Agfa Image Plate). In FIG. 7 (below), a profile of overall signal intensity $SI_{ges}$ is shown over a displacement path of 80 mm in x-direction, which cuts the cuvettes. On the far left in the profile, the acrylate glass base is reproduced in constant intensity. Next to it, on the right, is the streaky bacon, with decreasing intensity to about 35 mm. Next to it, on the right, is the measuring cuvette that contains 30 mg/ml of I (further drop in intensity). After a slight increase in the intensity, an area of reduced intensity by the absorption through the measuring cuvette follows with 100 mmol of Gd. In the x-coordinate range of about 65 to 75 mm, in turn there is an area in which only the streaky bacon is absorbed. On the far right, a renewed drop in intensity can be detected (x-coordinate range of about 80 mm), which can be attributed to the absorption of the x-ray radiation through the measuring cuvette that contains 5 mg/ml of I.

EXAMPLE 2

As an object under examination, a phantom was produced by the arrangement of two 1 cm plastic cuvettes as well as a plastic strip on an acrylate glass base. The cuvettes were filled with 0.5 mol of Gd/l (in the form of a gadolinium compound in aqueous solution) or with 0.47 mol of I/l (in the form of an iodine compound in aqueous solution).

First, in turn, an overall picture of the arrangement was taken with a phosphorus display (Agfa Image Plate). The details of the execution of the test are indicated in Example 1. The arrangement is shown in FIG. 8.

Overall signal intensity $SI_{ges}$ was recorded as a function of the x-movement of the phantom. The attenuation of the x-ray intensity by the plastic film, the measuring cuvette that contains iodine, and the measuring cuvette that contains gadolinum (from the left) are readily detectable.

This is also evident in particular from the profile of overall intensity $SI_{ges}$, which is plotted in parallel thereto and which was obtained with use of the measuring arrangement with an x-y-plotting table and a CZT detector. The profile is reproduced in FIG. 9. The profile was drawn up along the diagonal in the general view of FIG. 8 from the right top to the left bottom. In FIG. 10, x-ray spectra are shown at positions 30, 40 and 60 mm and in FIG. 11, the first derivatives of the signal intensities according to the energy (only the area up to 60 keV is shown to suppress effects on the characteristic emission lines from the spectra). The first derivatives reflect the increase in signal intensities as a function of the energy. It can be seen clearly how iodine and gadolinium differ from the background (curve at 30 mm) in the first derivatives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the foregoing and in the following examples, all temperatures are set forth uncorrected in degrees Celsius and, all parts and percentages are by weight, unless otherwise indicated.

The entire disclosures of all applications, patents and publications, cited herein and of corresponding German application No. 10347961.9, filed Oct. 10, 2003 and U.S. Provisional Application Ser. No. 60/512,764, filed Oct. 21, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An X-ray arrangement for imaging an object under examination that contains at least one opacifying element that comprises
    a. at least one x-ray radiation source that emits essentially polychromatic x-ray radiation with a continuous spectrum,
    b. at least one energy-dispersive detector for simultaneously detecting the intensity of x-ray radiation that gets through the object under examination at a given pixel at a first energy $E_1$, and the intensity of x-ray radiation that gets through said object under examination at the same pixel at a second energy $E_2$,
    c. at least one correlation unit for correlating the intensity of the detected x-ray radiation from said pixel of the object under examination at said first energy $E_1$ with the intensity of the detected x-ray radiation of the same pixel at said second energy $E_2$, and
    d. at least one output unit for visualizing the object under examination from the pixel signals obtained by correlation of the intensities, wherein one of the first energy $E_1$ and the second energy $E_2$ is above the energy of the K- or L-absorption edge of the opacifying element and the other is below said edge.

2. An X-ray arrangement according to claim 1, wherein the correlation unit has the following devices:
    e. a first storage unit, with which the intensities of individual pixels of the object under examination can be stored,
    f. a computing unit, with which the intensity of the detected x-ray radiation from a pixel of the object under examination at the first energy $E_1$ can be correlated with the intensity of the detected x-ray radiation from the same pixel at the second energy $E_2$,
    g. a second storage unit, with which the values that can be obtained from the intensities of an individual pixel by correlation can be intermediately stored.

3. An X-ray arrangement according to claim 1, wherein the intensities of the detected x-ray radiation from a pixel can be subtracted from one another or divided by one another with the correlation unit without taking logarithms or after logarithms are taken in advance, or wherein their derivatives can be formed according to the energy.

4. An X-ray arrangement according to claim 1, wherein the detector is a flat-bed detector.

5. An X-ray arrangement according to claim 1, wherein the detector is designed to pick up an individual pixel and is movable so as to be able to pick up all pixels.

6. An X-ray arrangement according to claim 1, wherein the detector has an array of detector sensors that are designed to pick up a pixel in each case and is movable so as to be able to pick up all pixels.

7. An X-ray arrangement according to claim 1, wherein the first energy $E_1$ and the second energy $E_2$ lie in an area that extends from energy values above to energy values below an absorption edge of the opacifying element.

8. An X-ray arrangement according to claim 1, wherein the first energy $E_1$ and the second energy $E_2$ lie in an area that extends from up to 5 keV below to up to 5 keV above the energy of the K- or L-absorption edge of the opacifying element.

9. An X-ray arrangement according to claim 1, wherein the opacifying element is an x-ray contrast medium and wherein the x-ray contrast medium contains at least one of bromine, iodine, barium, lanthanides or bismuth.

10. An X-ray arrangement according to claim 1, wherein the continuous spectrum of polychromatic x-ray radiation is an x-ray emission within the range of $\geqq 20$ keV-100 keV.

11. A method of x-ray contrast imaging of a patient comprising:
    a. administering an x-ray contrast medium containing an opacifying element to the patient,
    b. irradiating the patient with essentially polychromatic x-ray radiation with a continuous spectrum,
    c. simultaneously energy-dispersively detecting the intensity of the x-ray radiation that passes through the patient at a first energy $E_1$, and the intensity of the x-ray radiation that passes through the patient at a second energy $E_2$, d. correlating the intensity of detected x-ray radiation from a pixel of the patient under examination at said first energy $E_1$ with the intensity of the detected x-ray radiation of the same pixel at said second energy $E_2$, e. visualizing the patient from pixel signals that are obtained by correlation of the intensities, wherein x-ray radiation with a continuous spectrum is detected with an energy-dispersive detector, and wherein one of the first energy $E_1$ and the second energy $E_2$ is above the energy of the K- or L-absorption edge of the contrast medium and the other is below said edge.

12. A method according to claim 11, wherein the intensities of the x-ray radiation from a pixel are subtracted from one another or divided by one another with the correlation unit without taking logarithms or after logarithms are taken in advance, or wherein their derivatives are formed according to the energy.

13. A method according to claim 11, wherein said energy-dispersive detector is a flat-bed detector.

14. A method according to claim 11, wherein said energy-dispersive detector is designed to pick up an individual pixel and is movable so as to be able to pick up all pixels.

15. A method according to claim 11, wherein said energy-dispersive detector is an array of detector sensors that is designed to pick up a pixel in each case and said array is movable so as to be able to pick up all pixels.

16. A method according to claim 11, wherein the first energy $E_1$ and the second energy $E_2$ lie in a range that extends from up to 5 keV below to up to 5 keV above the absorption edge of the opacifying element.

17. A method according to claim 11, wherein said opacifying element x-ray contrast medium is at least one element that is bromine, iodine, barium, a lanthanide, or bismuth.

18. A method according to claim 11, wherein said x-ray contrast medium is administered enterally or parenterally.

19. A method according to claim 11, for specific graphic or quantitative display of a volume that contains said opacifying element.

20. A method according to claim 11, wherein said first energy $E_1$ and said second energy $E_2$ are within the range of from 3 keV above said K- or L-absorption edge of said contrast medium to 3 keV below said K- or L-absorption edge of said contrast medium.

21. A method according to claim 11, wherein one of said first energy $E_1$ and said second energy $E_2$ is within the range of 1-5 keV above said K- or L-absorption edge of said contrast medium, and the other of said first energy $E_1$ and said second energy $E_2$ is within the range of 1-5 keV below said K- or L-absorption edge of said contrast medium.

22. A method according to claim 11, wherein the intensities of the x-ray radiation from a pixel are measured over the range of ±2 keV relative to said absorption edge at narrow energy intervals of ±0.2 keV.

23. A method according to claim 11, wherein the continuous spectrum of polychromatic x-ray radiation is an x-ray emission within the range of $\geqq$0 keV-100 keV.

24. A method according to claim 23, wherein the continuous spectrum of polychromatic x-ray radiation is an x-ray emission within the range of $\geqq$15 keV-100 keV.

25. A method according to claim 23, wherein the continuous spectrum of polychromatic x-ray radiation is an x-ray emission within the range of $\geqq$17 keV-100 keV.

26. A method according to claim 23, wherein the continuous spectrum of polychromatic x-ray radiation is an x-ray emission within the range of $\geqq$20 keV-100 keV.

27. A method of x-ray contrast imaging of a patient comprising:

a) subjecting a patient containing at least one opacifying element to an irradiation of polychromatic x-ray radiation with a continuous spectrum, wherein said opacifying element is naturally present in said patient or is introduced into said patient by administration of an x-ray contrast medium, b) during said irradiation, energy-dispersively detecting at a plurality of pixels the intensity of the x-ray radiation that passes through the patient at a first energy $E_1$ and at a second energy $E_2$, wherein for each pixel a first energy $E_1$ and a second energy $E_2$ are detected during said irradiation, c) for each pixel, correlating the intensity of detected x-ray radiation for the pixel at said first energy $E_1$ with the intensity of the detected x-ray radiation of the same pixel at said second energy $E_2$, to generate a signal for each pixel, and d) visualizing the patient from the pixel signals obtained by correlation of the first energy $E_1$ and second energy $E_2$ intensities, wherein said irradiation of polychromatic x-ray radiation with a continuous spectrum is detected with an energy-dispersive detector, and wherein said first energy $E_1$ is above the energy of the K- or L-absorption edge of the opacifying element and said second energy $E_2$ is below said K- or L-absorption edge of the opacifying element.

28. A method according to claim 27, wherein said opacifying element is naturally present in said patient.

29. A method according to claim 27, wherein said opacifying element is introduced into said patient by administration of an x-ray contrast medium.

30. A method according to claim 27, wherein said first energy $E_1$ and said second energy $E_2$ are within the range of from 5 keV above said K- or L-absorption edge of said contrast medium to 5 keV below said K- or L-absorption edge of said contrast medium.

31. A method according to claim 30, wherein said first energy $E_1$ and said second energy $E_2$ are within the range of from 3 keV above said K- or L-absorption edge of said contrast medium to 3 keV below said K- or L-absorption edge of said contrast medium.

32. A method according to claim 30, wherein the continuous spectrum of polychromatic x-ray radiation is an x-ray emission within the range of $\geqq$20 keV-100 keV.

33. A method according to claim 27, wherein the intensities of the x-ray radiation from a pixel are measured over the range of ±2 keV relative to said absorption edge at narrow energy intervals of ±0.2 keV.

34. A method according to claim 27, wherein the continuous spectrum of polychromatic x-ray radiation is an x-ray emission within the range of $\geqq$20 keV-100 keV.

35. A method according to claim 27, wherein said energy-dispersive detector is a flat-bed detector in the form of a large-area arrangement of individual detector sensors, whereby said flat-bed detector can detect intensities from all pixels simultaneously.

36. A method according to claim 27, wherein said energy-dispersive detector is designed to detect only energy-dependent intensities from an individual pixel and is movable so as to be able to detect energy-dependent intensities from all pixels, whereby intensities of individual pixels are detected in succession.

37. A method according to claim 27, wherein said energy-dispersive detector is in the form of an array of detector sensors and said array is designed to detect energy-dependent intensities from a plurality of pixels, and said array is movable so as to be able to detect energy-dependent intensities from all pixels.

38. A method according to claim 27, wherein during b) the intensities below the absorption edge for all pixels are first detected, and then all the intensities above the absorption edge for all pixels are detected, or the intensities above the absorption edge for all pixels are first detected, and then all the intensities below the absorption edge for all pixels are detected.

39. A method according to claim 27, wherein the intensities are measured and correlated pixel by pixel.

40. An X-ray arrangement for imaging an object under examination comprising:
   a. at least one x-ray radiation source, that emits essentially polychromatic x-ray radiation with a continuous spectrum, for subjecting the object under examination to an x-ray exposure;
   b. at least one energy-dispersive detector for detecting the intensity of x-ray radiation that gets through the object under examination during said x-ray exposure at a plurality of pixels of the object under examination, wherein said detector simultaneously detects the intensity of x-ray radiation at a plurality of energy levels at each of said pixels,
   c. at least one correlation unit for correlating, for each pixel of the object under examination, the intensity of the detected x-ray radiation of the pixel at a first energy $E_1$ with the intensity of the detected x-ray radiation of the same pixel at a second energy $E_2$ to obtain a pixel signal from each pixel, and
   d. at least one output unit for visualizing the object under examination from the pixel signals obtained by correlation of the intensities achieved from the correlation unit.

41. An X-ray arrangement according to claim 40, wherein the object under examination contains at least one opacifying element, and wherein one of said first energy $E_1$ and said second energy $E_2$ is above the energy of the K- or L-absorption edge of the opacifying element and the other is below the energy of the K- or L-absorption edge of the opacifying element.

42. An X-ray arrangement according to claim 40, further comprising a first storage unit for storing the x-ray intensities detected for each of individual pixels of the object under examination, and a second storage unit for storing the pixel signals obtained from said correlation of the intensity of the detected x-ray radiation of each pixel at a first energy $E_1$ with the intensity of the detected x-ray radiation of the same pixel at a second energy $E_2$.

43. A method of x-ray contrast imaging of a patient comprising:
   a. subjecting the patient to an x-ray exposure by irradiating the patient with essentially polychromatic x-ray radiation with a continuous spectrum,
   b. simultaneously energy-dispersively detecting, with an energy-dispersive detector, the intensity of the x-ray radiation at a plurality of energy levels that passes through the patient during said x-ray exposure at a plurality of pixels,
   c. for each pixel, correlating the intensity of detected x-ray radiation from the pixel of the patient at a first energy $E_1$ with the intensity of the detected x-ray radiation from the same pixel at a second energy $E_2$ to generate a pixel signal from each pixel,
   d. forming an image of at least a portion of said patient from pixel signals obtained by correlation of the detected x-ray radiation intensities.

44. A method according to claim 43, further comprising administering an x-ray contrast medium containing an opacifying element to said patient before simultaneously detecting the intensity of the x-ray radiation at the plurality of energy levels,
   wherein one of said first energy $E_1$ and said second energy $E_2$ is above the energy of the K- or L-absorption edge of the opacifying element and the other is below the energy of the K- or L-absorption edge of the opacifying element.

* * * * *